United States Patent [19]

Talmage

[11] Patent Number: 4,673,654

[45] Date of Patent: Jun. 16, 1987

[54] COMPOSITION FOR DETERMINING PEROXIDASE-LIKE ACTIVITY OF HEMOGLOBIN

[75] Inventor: Joseph M. Talmage, Landing, N.J.

[73] Assignee: Warner-Lambert Company, Morris Plains, N.J.

[21] Appl. No.: 793,602

[22] Filed: Oct. 31, 1985

[51] Int. Cl.[4] .................... G01N 31/22; G01N 33/72; C12Q 1/28

[52] U.S. Cl. ....................... 436/66; 422/56; 422/57; 422/58; 422/61; 436/904; 435/28

[58] Field of Search ............... 422/56, 57, 58, 61; 436/66, 904; 128/638, 749, 759; 435/28

[56] References Cited

U.S. PATENT DOCUMENTS

| | | | |
|---|---|---|---|
| 2,290,436 | 7/1942 | Kamlet | 436/66 |
| 3,092,464 | 6/1963 | Adams, Jr. et al. | 436/66 |
| 3,853,472 | 12/1974 | Rittersdorf et al. | 422/56 |
| 3,859,341 | 1/1975 | Jonsson et al. | 435/28 |
| 4,071,318 | 1/1978 | Lam | 436/66 |
| 4,077,772 | 3/1978 | Geissler | 436/904 |
| 4,329,317 | 5/1982 | Detweiler et al. | 422/58 |
| 4,587,100 | 5/1986 | Amano et al. | 422/56 |

FOREIGN PATENT DOCUMENTS

| | | | |
|---|---|---|---|
| 0123868 | 7/1984 | European Pat. Off. | 436/66 |
| 2546252 | 4/1976 | Fed. Rep. of Germany | 422/56 |

*Primary Examiner*—S. Leon Bashore
*Assistant Examiner*—Lori-Ann Cody
*Attorney, Agent, or Firm*—Gary M. Nath; Howard Olevsky

[57] ABSTRACT

The invention provides a reagent composition for detecting peroxidase-like activity in aqueous media, particularly for determining occult blood in fecal matter "in-the-bowl". The reagents comprise a dry mixture of a 3, 3', 5, 5' -tetramethylbenzidine and an alkali metal perborate, such as sodium perborate, and preferably also including a strong organic carboxylic acid such as citric acid and a sequesterant for trace metals such as ethylenediaminetetraacetic acid. The composition can be made increasingly more stable by coating the tetramethylbenzidine and an antioxidant with a water soluble polymer and or film coating the sodium perborate with a coating at least partially soluble in water. The reagents are deposited in porous or holed matrices including adsorbent paper, gelatin and molded polysaccharide film.

11 Claims, No Drawings

COMPOSITION FOR DETERMINING PEROXIDASE-LIKE ACTIVITY OF HEMOGLOBIN

BACKGROUND OF THE INVENTION

This invention is concerned with a reagent composition and method for the detection of peroxidase activity. The invention is particularly concerned with the detection of pseudo-peroxidase activity of hemoglobin in occult blood present in fecal matter and other biological specimens.

Colon and rectal cancers affect over 100,000 persons in the United States each year. Early diagnosis and treatment of these cancers as well as cancers of other digestive organs can result in a cure rate of 80% to 90% of those affected. However, late diagnosis and treatment reduces the cure rate to 25% or less. Thus early detection of this disease in the digestive tract is critical to its successful treatment.

Most cancers of the digestive tract bleed to a certain extent even in their early stages giving rise to occult or hidden blood in fecal matter. It has been the goal of many researchers to develop methods and tests for determining the presence of this occult blood by detecting the peroxidase-like activity of hemoglobin in the blood. One of the most widely used indicator reagents for diagnosing occult blood is derived from an extract from the wood of certain species of trees of the Guaiacum genus native to the American tropics. The extract, termed guaiac, turns from essentially colorless to blue in the presence of hemoglobin and an oxidizing agent such as hydrogen peroxide.

The tests most widely used today can be divided into two basic categories: the "direct contact" type and the "in the bowl" type. In the "direct contact" type a small sample of the feces is contacted with a chromophoric reagent deposited on some form of carrier and it is observed if the reagent undergoes a color change. In the "in the bowl" type, the reagent(s) on a support or carrier is placed in the toilet water containing fecal matter to be tested and any color change is observed. An example of the first "direct contact" type is the "Hemoccult" test disclosed in U.S. Pat. No. 3,966,006 and marketed by Smith Kline Diagnostics of Sunnyvale, Calif. Briefly, the test employs an adsorbent white paper impregnated with a guaiac reagent encased in a special test slide having openable flaps on both sides of the test slide. To use the test slide, one must obtain a sample of fecal matter, smear it onto the guaiac-impregnated paper by opening the panel on one side of the test slide, and thereafter closing the panel. A panel on the opposite side of the test slide is then opened and a developing agent, which is a stabilized solution of hydrogen peroxide and denatured alcohol, is applied to the guaiac-impregnated paper. If occult blood is present in the fecal matter smeared on the opposite side of the paper, the product of the guaiac reaction will appear as a blue substance against the white paper background, providing a positive indication of the presence of blood in the fecal matter.

Although the test is suitable for use by physicians in their offices and by diagnostic laboratories, it is not the type of test that is readily adaptable for use by the ordinary person because of their adverse reaction to handling fecal matter and because of lack of skill in interpreting the results. As stated above, the test requires that a specimen of fecal matter be obtained. Normally, a specimen is obtained by procuring a sample on the end of a spatula or a wooden tongue depressor, which is then used to smear the specimen on the paper in the test slide. Once the sample is obtained and the test procedure completed, both the test slide and the spatula or depressor must be disposed of. Disposal of the used materials can and does present a physical problem to, if not an adverse psychological reaction for, the ordinary person. Thus, the ordinary person is not likely to use the test because of the uncleanly nature and because of the disposal problems associated with the used test slide and spatula or depressor. Additionally, the ordinary person does not necessarily have the skill required to analyze, and thus form accurate conclusions from the test results.

As an alternative, the ordinary person can initiate the test in his home and then forward the test slide to his physician or a laboratory for addition of the developing agent and analysis of the test. This procedure, however, requires cold storage of the test slide and specimen if there is a significant time lapse before the test can be completed. Certainly, the ordinary person does not wish to store a fecal specimen in his household refrigerator, normally the only cold storage available to him, until he can present the specimen to his physician or an appropriate laboratory. Thus, the general public is not likely to follow or comply with this alternative.

U.S. Pat. No. 4,473,079 provides a direct contact test for occult blood in feces including an oxidation reduction indicator such as gum guaiac or benzidine carried by a support, a solid oxygen releasing compound such as sodium perborate on a spreadable medium and an applicator for sampling the biological substance to be tested.

An "in-the-bowl" test for occult blood is disclosed in U.S. Pat. No. 2,838,377 to D. E. Fonner. The basic test reagents employed by Fonner are o-toluidine and benzidine. These reagents, in the presence of blood and other reactants, produce a dye visible to the naked eye. Although the Fonner test appears to be a solution to the problem of finding a viable home test for occult blood, it has not met with success for two reasons. First, the above-listed reagents are in themselves known to cause cancer and thus are not suitable for general public distribution. More importantly, the Fonner reagents have a relatively high rate of providing false indications of the presence of occult blood as a result of tap water impurities such as metals.

In U.S. Pat. No. 4,385,114 to Werner Guthlein et al there is provided a process for the detection and determination of peroxidatively active substances by contacting a sample with a 3,3',5,5'-tetraalkylbenzidine and hydrogen peroxide or a substance which reacts with hydrogen peroxide and evaluating the coloration production by the reaction. The method is applied particularly for the detection of blood and glucose in urine and for cholesterol and cholesterol esters in serum. The method is specifically applied by successively impregnating filter paper with a solution containing the peroxide component and a solution containing the benzidine compound. After drying, the test paper is dipped into a urine sample and any color change, e.g. blue-green is noted.

In U.S. Pat. No. 4,175,923 to W. G. Friend an in-the-bowl occult blood test is described in which the user must apply a hydrogen peroxide solution to a sheet of paper impregnated with gum guaiac. The sheet is then placed into the toilet bowl and observed for a color change. In U.S. Pat. No. 4,541,987 to Guadagno a granular chemical formulation of a guaiacol sulfonic acid and a monopersulfate is sandwiched in pockets between an adsorbent paper and a non-adsorbent paper. The product is used by laying the assembly on the surface of the toilet bowl water, adsorbent paper facing down, and observing any color changes that take place.

The present invention, on the other hand, provides a dry, granular and stable reagent for the detection of occult blood in fecal matter in aqueous media, i.e. "in the bowl" in which all reactive components are mixed together and no reaction takes place until the reagent is wetted by the water. A sequesterant for the heavy metals found in household water supplies may also be included.

SUMMARY OF THE INVENTION

In brief, the invention comprises a dry, granular and highly stable reagent for the detection of occult blood in fecal matter or in other biological substrates in aqueous media comprising a 3,3',5,5'-tetramethylbenzidine and an alkali metal perborate such as sodium perborate which releases peroxide on contact with water. A strong organic carboxylic acid and a sequesterant for heavy metals may also be included. The dihydrogen sulfate form of the tetramethylbenzidine is preferably employed because of its higher stability than the free amine.

The instant inventive concept, like those of the prior art, are based on the detection of pseudo-peroxidase activity present in hemoglobin and biological fluids. This peroxidase-like activity, also referred to as catalytically active substances, in the case of blood are identified in hemoglobin. These substances belong to the general class of hemoproteins, conjugate proteins all of which have the same prosthetic group, iron protoporphyrin or haem. This prosthetic group has the ability to catalyze the transfer of oxygen from an oxygen source to an acceptor which in turn becomes oxidized. The acceptor is a colorless precursor until it becomes oxidized wherein the oxidized form indicates the presence of the peroxidase activity by color formation.

In order to achieve long term stability of the reagent composition, the 3,3',5,5'-tetramethylbenzidine is preferably coated with a water soluble polymeric material such as polyvinylpyrolidone in the presence of an antioxidant on a water soluble granular material such as sucrose or sodium sulfate prior to mixing with the other ingredients of the formulation. This prevents the 3,3',5,5'-tetramethylbenzidine from reacting with the perborate prior to contact with the blood containing sample. The stability of the compositions can be further enhanced by film coating the perborate with a polymeric coating at least partially soluble in water. It has been found that a mixture of ethyl cellulose and hydroxypropylmethyl cellulose provides an excellent coating. Water soluble and hygroscopic fillers may be employed in admixtures with the compositions such as mannitol, sorbitol and sodium sulfate.

The composition is produced in granular form and can be packaged in pockets of a biodegradable, floatable matrix such as tissue paper, or in perforated gelatin capsules, or in a cavity of a clear, cast, biodegradable material such as pullulan backed with paper. Pullulan is a commercially available triglucopolysaccharide obtained from Hayashibara Biochemical Laboratories, Inc. After defecation into a toilet bowl, the reagent composition in its package is placed into and floats on the surface of the water in the toilet bowl. Any blood present in the toilet bowl water is detected by the formation of a blue color in the reagent formulation.

DETAILED DESCRIPTION OF THE PREFERRED EMBODIMENTS

In the present invention all the ingredients necessary for the performance of the test for occult blood are included in the reagent composition as a dry mixture requiring no addition or mixing of reagents prior to performing the test as those of the prior art. No reaction takes place until the reagent is wetted by the toilet bowl water. The matrices containing the reagents as will be described hereafter are designed so that only a small portion of the water penetrates the reagents within the time necessary to perform the test, i.e. a few seconds to two minutes, thus providing a high concentration of reagents and therefore a sensitive test for occult blood.

The chromogen in the test reagent of the invention is 3,3',5,5'-tetramethylbenzidine, a non-carcinogenic leuco dye capable of being oxidized to a blue dye by hydrogen peroxide in the presence of the peroxidase activity of certain components of blood, particularly hemoglobin. The alkali metal perborate is preferably sodium perborate monohydrate which is a heat stable compound which releases hydrogen peroxide when added to water. Thus when 3,3',5,5'-tetramethylbenzidine and sodium perborate monohydrate are combined in the presence of water and peroxidatively active hemoglobin in blood, the tetramethylbenzidine is oxidized to a blue-colored tetramethyl derivative of benzidine. A stable, dry, strong, water soluble acid is added to the reagent formulation to adjust the pH of the reagent to the desired range when wetted, that is, between about pH 5 and about pH 7. Such acid is preferably anhydrous citric acid. In order to suppress metal catalysis by trace metals found in household water supplies which may give a false positive reaction, a sequesterant such as ethylenediaminetetraacetic acid or its sodium salts is added to the reagent.

Although 3,3',5,5'-tetramethylbenzidine as the free amine may be employed in the invention, a more stable derivative is 3,3',5,5'-tetramethylbenzidine dihydrosulfate. The dihydrochloride salt of tetramethylbenzidine cannot be used because, in the presence of peroxide, the hydrochloride is converted to hypochlorite which oxidizes tetramethylbenzidine to the blue dye in the absence of blood. In order to prevent the reaction of the tetramethylbenzidine and the perborate in the presence of moisture for example, the reagents of the invention are produced and maintained in a dry state until use. The stability of the reagent is further enhanced however, by treating either the tetramethylbenzidine or the peroxide source or both to render them virtually non mutually reactive until they are used for the test. As a further treatment of the tetramethylbenzidine a composition containing tetramethylbenzidine and an antioxidant is coated with a water soluble polymer on an inert, water soluble, granular material such as sucrose. Such a composition is prepared by dissolving an antioxidant such as butylatedhydroxytoluene (BHT) the tetramethylbenzidine, and polyvinylpyrolidone in chloroform. This solution is added to granulated sucrose and the chloroform removed by heating with constant stirring.

As a further treatment of the perborate it may be film coated on a fluidized bed with a mixture of ethyl cellulose and hydroxypropylmethyl cellulose at a ratio of approximately 10% coating to 90% sodium perborate monohydrate before addition to the other ingredients. The coating is water soluble and allows the perborate to react with water for testing for occult blood.

A water soluble and preferably hygroscopic filler such as mannitol, sorbitol, sodium sulfate and the like may be added to the composition to help absorb water rapidly and thus to promote a rapid test reaction.

The reagents are prepared by mixing all components thereof in a blending device for example. Preferably however, the tetramethylbenzidine, acid, sequesterants and fillers, if any, are first mixed and the perborate added thereto.

In general, the amount of 3,3',5,5'-tetramethylbenzidine or its dihydrosulfate salt should constitute from about 0.5 to 5% of the formulation. The sodium perborate monohydrate should constitute about 5% to 30% of the total reagent. The acid concentration can vary between 1% and 5% by weight of the total reagent and the sequesterant can vary between 5% and 30% by weight. Fillers and other materials employed to increase the stability of the reagent constitute the remainder.

Although the above described reagent is particularly useful for in-the-bowl determination of occult blood in fecal matter it can also be used to determine the peroxidative activity of any biological specimen in aqueous media.

Positive and negative controls may also be included. The positive control contains the basic ingredients and dried whole blood, hemoglobin, or hematin to assure the user that the reagent chemistry is working. The negative control eliminates the peroxide source and insures that there are no chemicals in the toilet bowl water that will cause the reagents to yield a positive test.

The matrix, containing the granular reagent, can be of anyone of three basic configurations. The granular reagents can be contained in pockets of a laminated biodegradable material such as paper, in clear, biodegradable gelatin capsules containing perforations to allow for the influx of water, or in clear wells molded from a biodegradable polymer, e.g., a polysaccharide such as pullulan, backed with an adsorbent paper. The size of the reagent containing matrix may be of any size consistent with economies and the water surface in a toilet bowl. Both the paper and clear, molded polysaccharide matrices may have multiple sections containing test and control reagent granules. Alternatively, the control reagents may be prepared separately on the paper and polysaccharide matrices.

The reagent-containing matrix is placed in the bowl containing feces suspected of containing occult blood. A blue color change of the reagent with the observance of the same color change for the positive control and no color change for the negative control indicates blood. The change in color usually will take no more than a few minutes.

In order to more fully describe the present invention the following Examples are given. All percentages are based on total weight unless otherwise indicated.

EXAMPLE 1

In this Example a reagent composition was prepared using the following ingredients.

| Ingredient | Wt. % |
| --- | --- |
| Mannitol U.S.P. | 69% |
| Citric Acid Anhydrous | 14% |
| Tetrasodium EDTA.2H$_2$O | 2% |
| Tetramethylbenzidine | 1% |
| Sodium Perborate Monohydrate | 14% |

The formulation was prepared by blending the mannitol, citric acid, EDTA, and tetramethylbenzidine in a Hobart Mixer for 10 minutes on speed 1 then adding the sodium perborate and blending for an addition 2 minutes.

EXAMPLE 2

This Example illustrates the preparation of a more stable reagent formulation employing tetramethylbenzidine dihydrosulfate instead of the free amine. Stability of the reagent was even further enhanced in this Example by film coating the sodium perborate monohydrate on a fluidized bed with a mixture of ethyl cellulose (40% by weight) and hydroxypropylmethyl cellulose (60% by weight) at a ratio of approximately 10% coating to 90% sodium perborate monohydrate before addition to the other ingredients. The composition is set forth below.

| Ingredient | Wt. % |
| --- | --- |
| Mannitol U.S.P. | 67% |
| Citric Acid Anhydrous | 14% |
| Tetrasodium EDTA.2H$_2$O | 2% |
| Tetramethylbenzidine.2H$_2$SO$_4$ | 1% |
| Film Coated Sodium Perborate Monohydrate | 16% |

EXAMPLE 3

In this Example the tetramethylbenzidine dihydrosulfate was made stable by coating it and an antioxidant with a water soluble polymer on sucrose as an inert, water soluble material. Such composition (sucrose-tetramethylbenzidine granulation) was prepared by dissolving 1 gram of butylatedhydroxytoluene, 1 gram of tetramethylbenzidine, and 4 grams of polyvinylpyrolidone in 40 ml. of chloroform. The solution was added to 94 grams of granulated sucrose and the chloroform removed by heating with constant stirring. The resulting granulation was free flowing and contained 1% tetramethylbenzidine. This granulation was used to prepare the test formulation described below. Mannitol was not used in this formulation.

| Ingredient | Wt. % |
| --- | --- |
| Sucrose-tetramethylbenzidine Granulation | 52% |
| Citric Acid Anhydrous | 21% |
| Film Coated Sodium Perborate Monohydrate | 26% |
| Tetrasodium EDTA.2H$_2$O | 1% |

EXAMPLE 4

In this Example, a positive control formulation was prepared by adding hemoglobin to a test formulation as shown below:

| Ingredient | Wt. % |
| --- | --- |
| Mannitol U.S.P. | 67% |

-continued

| Ingredient | Wt. % |
| --- | --- |
| Citric Acid Anhydrous | 13.98% |
| Tetrasodium EDTA.2H$_2$O | 2% |
| Tetramethylbenzidine:2H$_2$SO$_4$ | 1% |
| Film coated Sodium Perborate Monohydrate | 16% |
| Hemoglobin | 0.02% |

EXAMPLE 5

In this Example, a negative control formulation was prepared by blending filler, tetrasodium EDTA, sodium citrate and tetramethylbenzidine dihydrosulfate as shown below:

| Ingredient | Wt. % |
| --- | --- |
| Mannitol U.S.P. | 61% |
| Citric Acid Anhydrous | 11% |
| Sodium Citrate U.S.P. | 25% |
| Tetrasodium EDTA.2H$_2$O | 2% |
| Tetramethylbenzidine.2H$_2$SO$_4$ | 1% |

EXAMPLE 6

Each of the dry, granular compositions as described in Examples 1 to 5, are incorporated into the following test matrices: A. Paper Matrix, B, Gelatin Capsules and C, Clear Molded Polysaccharide Film at 0.1 g to 0.5 g per matrix.

A.

Paper Matrix

For each device to be made, two sheets of adsorbent paper were cut to size. One sheet was masked in the areas where the granular compositions are to be placed and sprayed with a pressure sensitive spray adhesive. The masks are removed and 0.1 g to 0.5 g of chemical formulation deposited. The second sheet of paper is then layered atop the first containing the contact adhesive and pressed in place. Each formulation was thus laminated between the pieces of paper in discrete, well defined areas. In the same manner papers containing the positive and negative controls were prepared. The resulting devices including controls are placed on top of toilet bowl water containing fecal matter, and any color changes due to the presence of occult blood are observed noting the positive and negative controls.

B.

Gelatin Capsules

Number 0, 00, or 000 clear, hard gelatin, two piece capsules are used. Several random small holes are made in each capsule by puncturing with a No. 27 hypodermic syringe needle heated in a flame. The capsules may be coated with a thin film of polysorbate to prevent the formulation from spilling out. The capsules are opened, filled about half way with each formulation and closed. In the same manner the positive and negative controls are incorporated into capsules. The capsules are used by depositing in toilet bowl water containing fecal matter and observing any color change which takes place noting positive and negative controls. The clarity of the capsules makes any color change clearly discernable to the user.

C.

Clear, Molded Polysaccharide Film

An aqueous solution of the polysaccharide (pullulan) is poured into a suitable mold and placed in an oven at 40° C. The resulting clear, formed tray is removed from the mold and 0.1 g to 0.5 g of each formulation is placed into the wells. A piece of adsorbent paper is sprayed with a contact adhesive and pressed firmly on the tray. In the same manner positive and negative controls are incorporated into the wells. The formulations are thus isolated in the wells and can be used for detecting occult blood in toilet bowl water by placing the assembly, paper side down, in the water. The clarity of the polysaccharide film enhances the user's ability to discern any color changes taking place.

The invention being thus described, it will be obvious that the same may be varied in many ways. Such variations are not to be regarded as a departure from the spirit and scope of the invention and all such modifications are intended to be included within the scope of the following claims.

I claim:

1. A reagent for the determination of peroxidase-like activity in aqueous media comprising:
   (a) a 3,3',5,5'-tetramethylbenzidine coated with a water soluble polymer on an inert water soluble material; and
   (b) an alkali metal perborate.

2. The reagent of claim 1 which further comprises an antioxidant, butylatedhydroxytoluene.

3. The reagent of claim 1 wherein said water soluble polymer is polyvinylpyrolidone.

4. The reagent of claim 1 wherein said water soluble polymer is sucrose.

5. The reagent of claim 1 which further comprises citric acid.

6. The reagent of claim 1 which further comprises ethylenediaminetetraacetic acid or salt thereof.

7. The reagent of claim 1 which further comprises a water soluble filler.

8. The reagent of claim 7 wherein said filler is mannitol.

9. A laminate of sheets of adsorbent paper containing therebetween the reagent of claim 1.

10. A gelatin capsule having holes containing the reagent of claim 1.

11. A molded polysaccharide film having a plurality of wells containing the reagent of claim 1.

* * * * *